(12) United States Patent
Geffroy-Hyland et al.

(10) Patent No.: US 8,394,394 B2
(45) Date of Patent: Mar. 12, 2013

(54) MOUSSE FORMULATIONS

(75) Inventors: Nathalie Geffroy-Hyland, Franconville (FR); Mohamed Kanji, Edison, NJ (US); Hy Si Bui, Piscataway, NJ (US)

(73) Assignee: L'Oréal (FR)

( * ) Notice: Subject to any disclaimer, the term of this patent is extended or adjusted under 35 U.S.C. 154(b) by 853 days.

(21) Appl. No.: 11/138,940

(22) Filed: May 26, 2005

(65) Prior Publication Data

US 2005/0265943 A1 Dec. 1, 2005

Related U.S. Application Data

(60) Provisional application No. 60/574,652, filed on May 26, 2004.

(51) Int. Cl.
*A61K 8/02* (2006.01)
*A61Q 5/12* (2006.01)

(52) U.S. Cl. .................................. 424/401; 424/70.12

(58) Field of Classification Search .................. None
See application file for complete search history.

(56) References Cited

U.S. PATENT DOCUMENTS

| | | | |
|---|---|---|---|
| 3,418,353 A | 12/1968 | Brown, Jr. | |
| 3,439,088 A | 4/1969 | Edman | |
| 3,818,105 A | 6/1974 | Coopersmith | |
| 4,980,167 A | 12/1990 | Harashima et al. | |
| 5,015,469 A | 5/1991 | Yoneyama et al. | |
| 5,266,321 A | 11/1993 | Shukuzaki et al. | |
| 5,330,747 A | 7/1994 | Krzysik | |
| 5,492,945 A | 2/1996 | Morita et al. | |
| 5,538,793 A | 7/1996 | Inokuchi et al. | |
| 5,589,165 A | 12/1996 | Yoshida et al. | |
| 5,599,533 A | 2/1997 | Stepniewski et al. | |
| 5,654,362 A | 8/1997 | Schulz, Jr. et al. | |
| 5,676,938 A | 10/1997 | Kimura et al. | |
| 5,750,098 A | 5/1998 | LeGrow et al. | |
| 5,759,529 A | 6/1998 | LeGrow et al. | |
| 5,760,116 A | 6/1998 | Kilgour et al. | |
| 5,830,527 A | 11/1998 | Vickers et al. | |
| 5,849,314 A | 12/1998 | Dobkowski et al. | |
| 5,919,467 A | 7/1999 | Jenkins et al. | |
| 5,925,338 A | 7/1999 | Karassik et al. | |
| 5,945,471 A | 8/1999 | Morita et al. | |
| 5,972,318 A | 10/1999 | Bara | |

(Continued)

FOREIGN PATENT DOCUMENTS

EP 0 295 886 12/1988
EP 0 381 166 8/1990

(Continued)

OTHER PUBLICATIONS http://www.merriam-webster.com/dictionary/pilling Accessed on Apr. 25, 2008.*

(Continued)

*Primary Examiner* — Brian Gulledge
(74) *Attorney, Agent, or Firm* — Lerner, David, Littenberg, Krumholz & Mentlik, LLP (57) ABSTRACT

The present invention relates to a cosmetic base which includes an anhydrous mixture of an effective amount of at least one first silicone elastomer; an effective amount of at least one second silicone elastomer; at least one non-aqueous solvent; and an effective amount of at least one water insoluble structuring agent which is compatible with said solvent and which has a melting point of between about 45 and about 95° C. The cosmetic base may be used in a cosmetic composition which also includes a pigment. Methods of making these cosmetic formulations are also described.

27 Claims, 1 Drawing Sheet

U.S. PATENT DOCUMENTS

| | | | |
|---|---|---|---|
| 6,027,738 | A | 2/2000 | Stepniewski et al. |
| 6,177,091 | B1 | 1/2001 | Bara et al. |
| 6,184,277 | B1 | 2/2001 | Bara |
| 6,235,292 | B1 | 5/2001 | Bara et al. |
| 6,350,440 | B1 | 2/2002 | Koini et al. |
| 6,399,081 | B1 | 6/2002 | Nakanishi et al. |
| 6,444,745 | B1 | 9/2002 | Kilgour et al. |
| 6,475,500 | B2 * | 11/2002 | Vatter et al. .................. 424/401 |
| 6,479,686 | B2 | 11/2002 | Nakanishi et al. |
| 6,503,516 | B1 | 1/2003 | Van Liew et al. |
| 6,524,598 | B2 * | 2/2003 | Sunkel et al. ................. 424/401 |
| 6,589,517 | B1 | 7/2003 | McKelvey et al. |
| 6,696,049 | B2 | 2/2004 | Vatter et al. |
| 2001/0014312 | A1 | 8/2001 | Nakanishi et al. |
| 2001/0033826 | A1 | 10/2001 | Roulier et al. |
| 2002/0028223 | A1 | 3/2002 | Vatter et al. |
| 2002/0058053 | A1 | 5/2002 | Nakanishi et al. |
| 2002/0081323 | A1 | 6/2002 | Nakanishi et al. |
| 2002/0102225 | A1 | 8/2002 | Hess et al. |
| 2002/0106385 | A1 | 8/2002 | Vatter et al. |
| 2002/0114771 | A1 | 8/2002 | Nakanishi |
| 2002/0114773 | A1 | 8/2002 | Kanji et al. |
| 2002/0131947 | A1 | 9/2002 | Nakanishi |
| 2002/0141958 | A1 | 10/2002 | Maio et al. |
| 2002/0159964 | A1 | 10/2002 | Nakanishi et al. |
| 2003/0039620 | A1 | 2/2003 | Rodriguez et al. |
| 2003/0049212 | A1 * | 3/2003 | Robinson et al. ................. 424/59 |
| 2003/0049216 | A1 | 3/2003 | Jose et al. |
| 2003/0078172 | A1 * | 4/2003 | Guiramand et al. .......... 510/135 |
| 2003/0103918 | A1 | 6/2003 | Jose et al. |
| 2003/0147830 | A1 | 8/2003 | Phillips et al. |
| 2003/0161848 | A1 | 8/2003 | Ferrari et al. |
| 2003/0165546 | A1 | 9/2003 | Resch et al. |
| 2004/0018163 | A1 | 1/2004 | Yu |
| 2004/0228819 | A1 | 11/2004 | Rabe et al. |

FOREIGN PATENT DOCUMENTS

| | | |
|---|---|---|
| EP | 0 827 983 | 3/1998 |
| EP | 0 958 804 | 11/1999 |
| EP | 0958085 | 11/1999 |
| EP | 1 062 959 | 12/2000 |
| EP | 1 095 959 | 5/2001 |
| EP | 1 164 172 | 12/2001 |
| EP | 1 213 011 | 6/2002 |
| EP | 1 213 316 | 6/2002 |
| EP | 1 224 928 A | 7/2002 |
| EP | 1 457 192 A | 9/2004 |
| JP | 3264510 | 11/1991 |
| JP | 9071509 | 3/1997 |
| JP | 9315936 | 12/1997 |
| JP | 10130120 | 5/1998 |
| JP | 2001114623 | 4/2001 |
| WO | WO-95/25499 | 9/1995 |
| WO | WO-95/25503 | 9/1995 |
| WO | WO-98/34747 | 8/1998 |
| WO | WO-00/61076 | 10/2000 |
| WO | WO-1 062 944 | 12/2000 |
| WO | WO-02/03931 | 1/2002 |
| WO | WO-02/03932 | 1/2002 |
| WO | WO-02/03933 | 1/2002 |
| WO | WO-02/03935 | 1/2002 |
| WO | WO-02/03950 | 1/2002 |
| WO | WO-02/03952 | 1/2002 |
| WO | WO-02/092047 | 11/2002 |
| WO | WO-03/042221 | 5/2003 |

OTHER PUBLICATIONS http://dictionary.reference.com/search?q=Pilling&r=66 Accessed on Apr. 25, 2008.*
Chocolate Mousse (Formulation 00650) Information From Dow Corning®.
International Search Report, PCT/US05/018477, Dated Oct. 10, 2005.
Aube Mousse Cheeks KAO Sofina (KAO) product label information.
Max Factor International Visual Magic, Max Factor (Procter & Gamble) product label information.
Nina Ricci Mousse de Blush, Nina Ricci (PUIG) product label information.
Ettusais Souffle Cheek Color, Ettusais (Shiseido) product label information.
Ultima II Glowtion Highlighting Souffle, Ultima II (Revlon), product label information.
Clarins White Plus Lightening Foundation With plant extracts, Clarins product label information.
Ayura Pearl Whipped Shadow, Ayura Lab K.K. (Shiseido) product label information.

* cited by examiner

MOUSSE FORMULATIONS

CROSS-REFERENCE TO RELATED APPLICATIONS

This application claims the benefit of the filing date of U.S. Provisional Patent Application No. 60/574,652 filed May 26, 2004, the disclosure of which is hereby incorporated herein by reference.

BACKGROUND OF THE INVENTION

People in general and women in particular spend a good deal of time wearing cosmetic products. These products are sometimes colored with pigments or dyes or they may be uncolored. As important as the actual color of the product may be, if indeed it is colored, the ease of application, feel, coverage and wear characteristics are critical to maintaining customer acceptance. Therefore, while great strides have been made to improve various properties cosmetic properties, even incremental advances in the feel of a cosmetic product on the skin, particularly over long periods of time, can be very important to a product's success.

One class of products that has been introduced, particularly in foundations, eye shadows and blushes, are mousse or souffle type products. These products contain a relatively high degree of aeration and a light, creamy, almost spongy feel tactilely. However, not only is this category susceptible to improvement in terms of its feel, wear and coverage characteristics, but its manufacturing as well. A number of products are already on the market including Nina Ricci Mousse De Blush; Aube Mousse Cheeks; Ettusais Souffle Cheek Color; Estee Lauder Pure Color Cool Eye Mousse; Ayura Pearl Whipped Shadow; and Clarins White Plus Lightening Foundation with plant extracts.

Improvements can nonetheless be made, particularly in the processability of materials. When various mousse type formulations are produced without, for example, proper selection of the elastomers and the use of a structuring agent, it may be difficult to have them be both sufficiently pumpable and processable to fill containers and yet set up quickly enough and rigidly enough so that they do not take on undesirable shapes during set up, packaging and storage. Once the material is applied to the lumen of a container, it should fill the lumen completely and maintain the desired shape. Second, formulations based only on elastomers can exhibit variations, particularly in terms of their tactile sensation and spreading characteristics from batch to batch. Formulations that could solve these issues in terms of both cosmetic properties to the wearer and processing advantages are therefore highly desirable.

SUMMARY OF THE INVENTION

In one aspect of the present invention, there is provided a cosmetic base comprising an anhydrous mixture of an effective amount of at least one first elastomer (also referred to herein as a first silicone elastomer), preferably a nonemulsifying silicone elastomer capable of forming a sustainable gel and/or pilling; an effective amount of at least one second elastomer (also referred to herein as a second silicone elastomer), generally a nonemulsifying silicone elastomer incapable of forming a sustainable gel and often one that can exist as a spherical powder; at least one non-aqueous or anhydrous silicone based solvent and an effective amount of at least one water insoluble structuring agent, which is compatible with the solvent. Preferably, the structuring agent has a melting point of between about 45 and about 90° C.

In accordance with another aspect of the present invention, there is provided a cosmetic composition that includes one or more of the cosmetic bases identified immediately above and, in addition, at least one pigment. Methods of making these cosmetic formulations are also contemplated. It has been found that by selecting specific elastomers, structuring agents and solvents, one can obtain a mousse or souffle formulation with extremely desirable properties. These formulations have a springy, luxuriant feel, as well as excellent spreading and covering properties. They often exhibit good substantivity, excellent wear, and when pigmented, excellent color. The formulations of the present invention are efficiently processable and can be placed into cosmetic containers or other receptacles where they can maintain a shape with little or no flow after packaging. In particular, many of the formulations in accordance with the present invention can be pumped and processed in a generally fluid form and poured into a container wherein it efficiently fits the lumen of the package. Many of these formulations set up quickly and maintain their shape. Moreover, many of these formulations provide very good reproducibility from batch to batch, much more so than that which would likely result from formulations without each of these components. Similarly, many of the formulations in accordance with the present invention afford superior control of feel from batch to batch. Particularly preferred cosmetic compositions in accordance with one aspect of the present invention are colored cosmetics, such as foundation, blush, eye makeup and the like which are in the form of a topical mousse.

In one embodiment, the present invention is a cosmetic base comprising: an anhydrous mixture of an effective amount of at least one first silicone elastomer; an effective amount of at least one second silicone elastomer; at least one non-aqueous solvent; and an effective amount of at least one water insoluble structuring agent which is compatible with said solvent and which has a melting point of between about 45 and about 95° C. In another embodiment, the at least one first silicone elastomer is present in an amount of between about 0.1 and about 40% by weight of dry elastomer based on the weight of the base. In another embodiment, the at least one first silicone elastomer is selected from the group consisting of DC9040, SFE839, KSG6, KSG15, KSG16, KSG17, KSG18, and Velvesil as well as mixtures thereof. In yet another embodiment, the at least one second silicone elastomer is present in an amount of between about 0.1 and about 40% by weight of dry elastomer based on the weight of said base. In still another embodiment, both the first and second elastomers are present in amounts of between about 0.1 and about 40% by weight of dry elastomer based on the weight of the base, respectively.

In an embodiment, the second silicone elastomer is non-sustainable and nonpilling and in yet another embodiment, it is spherical. One particularly interesting second silicone elastomer is DC9506, known as dimethicone/vinyldimethicone crosspolymer, or DC 9701 and mixtures thereof.

In still another embodiment, any of the cosmetic bases described above, the water insoluble structuring agent is present in an amount of between about 0.1 and about 20% by weight based on the weight of the base.

Another embodiment is a cosmetic composition comprising: a cosmetic base including an anhydrous mixture of an effective amount of at least one first silicone elastomer; an effective amount of at least one second silicone elastomer; at least one non-aqueous silicone solvent; an effective amount of at least one water insoluble structuring agent which is compatible with said solvent; and at least one pigment. In one embodiment, the pigment is provided in an amount of up to 60% by weight of the composition, the first and second silicone elastomers is present in an amount of between about 0.1 and about 40% by weight of dry elastomer based on the weight of the base, respectively, and the second silicone elastomer is preferably nonsustainable and nonpilling. In one embodiment, the cosmetic composition wherein the water insoluble structuring agent is present in an amount of between about 0.1 and about 20% by weight based on the weight of the base.

In any of the forgoing embodiments, either the cosmetic base, the cosmetic composition or both will have certain rheological properties such that $G'(\omega)/G''(\omega)$ also referred herein as G'/G", (both expressed as $\omega$=frequency=100 radians per second (100 rad/sec)), ranges from about 1 to about 100, and in another embodiment, from about 1.2 to about 50. In yet another embodiment, G'/G" ranges from about 1.3 to about 25 and in still another embodiment, from about 1.5 to about 7. When expressed in terms of G'/G" (both measured at $\omega$=frequency=0.1 rad/sec), the ratio of about 0.1 to about 100 is observed. In one embodiment, that ratio may be about 1 to about 50, and in another embodiment, from about 2.5 to about 25.

In yet another embodiment of the aspect, the G'/G" at 0.1 rad/sec is from about 3.0 to about 4.0. $G'(\omega)$ is also known as the storage or elastic modulus and $G''(\omega)$ is the loss modulus.

It is particularly desirable, but not necessary, that the formulations of the invention include, for example, both a ratio of G'/G" at 100 rad/s of about 1 to about 100 and a G'/G" at 0.1 rad/s of about 0.1 to about 100. In another embodiment, G'/G" at 100 rad/s is about 1.2 to about 50 and G'/G" at 0.1 rad/s is about 1 to about 50. In yet another embodiment, G'/G" at 100 rad/s is about 1.3 to about 25, while G'/G" at 0.1 rad/s is about 2.5 to about 25. In still another embodiment, G'/G" at 100 rad/s is about 1.5 to about 7 and G'/G" at 0.1 rad/s is about 3 to about 4.

The real or in-phase viscosity $\eta'(\omega)$ is also defined using loss modulus using the following equation: $\eta'(\omega)=G''(\omega)/\omega$. In one embodiment where frequency ($\omega$) is 0.1 rad/s, dynamic viscosity ranges from about $1\times10^1$ to about $9\times10^6$ Pa·s. (Pascal seconds). In another embodiment, dynamic viscosity ranges from about $1\times10^2$ to about $5\times10^6$ Pa·s. and in yet another embodiment, from about $1\times10^3$ to about $1\times10^6$ Pa·s. In still another embodiment, dynamic viscosity ranges from about $2\times10^3$ to about $1\times10^5$ Pa·s.

In any of the cosmetic compositions described above, there will be a hardness of between about 10 and about 50 g.

In one embodiment of the present invention, there is provided either a cosmetic base or a cosmetic composition either of which include a cosmetic base comprising an anhydrous mixture of an effective amount of at least one first gellable silicone elastomer. In one embodiment, the amount of this first elastomer ranges from about 0.1 to about 40% by weight of dry elastomer. That means that amount of the base or composition is the elastomer, based on the dry weight of the elastomer, excluding solvents and the like. They also include an effective amount of at least one second silicone elastomer wherein said second silicone elastomer is nonsustainable and nonpilling. In one embodiment, this second elastomer is present in an amount of about 0.1 to about 40% by weight of dry elastomer. The base and/or composition also includes at least one non-aqueous solvent; and an effective amount of at least one water insoluble structuring agent which is compatible with said solvent and which has a melting point of between about 45 and about 95° C. For any of these embodiments, at least one of G'/G", measured at a frequency of 100 rad/s ranges from about 1 to about 100, G'/G", measured at a frequency of 0.1 rad/s ranges from about 0.1 to about 100 or the dynamic viscosity ranges from about $1\times10^1$ to about $9\times10^6$ Pa·s. In another embodiment, the base or composition is characterized by at least two of these three properties and in yet another embodiment, the base and/or composition will satisfy all three.

DETAILED DESCRIPTION

Figure 1:
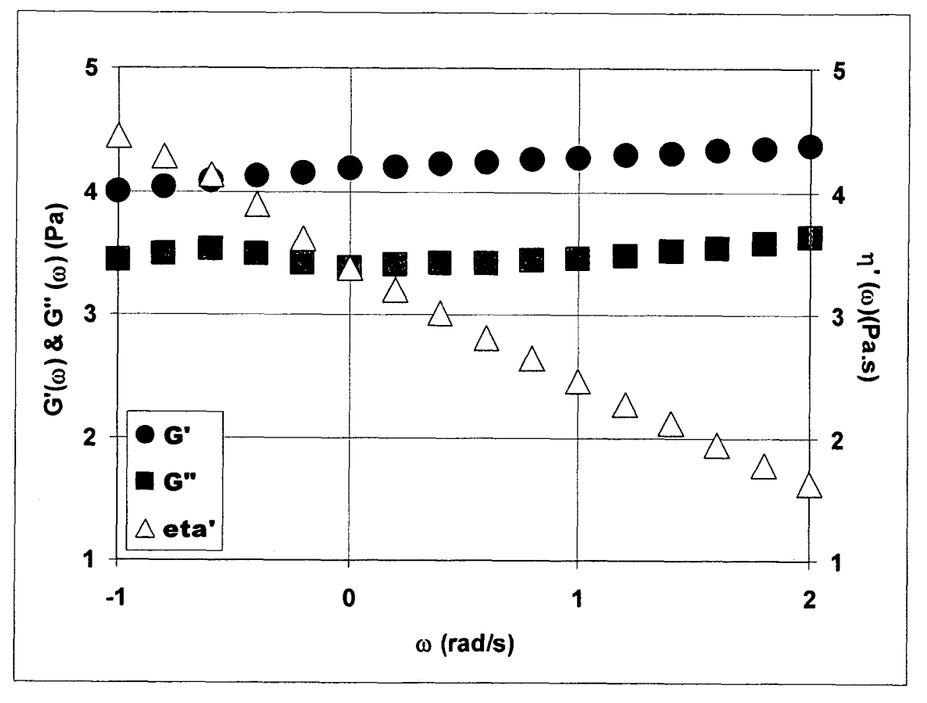
FIG. 1 is a graph showing $G'(\omega)$, $G''(\omega)$ and $\eta'(\omega)$ for a cosmetic composition (a mousse) in accordance with the present invention and Example 2.

As used herein, "comprising" is open-ended and meant to include the recited elements and any other elements. The term "between" includes the endpoints. Unless stated otherwise, all measurements are in metric units taken at room temperature (20° C.), and all temperatures reported herein are in degrees Celsius.

"Formulation" as used herein means a cosmetic base or a cosmetic composition. A "cosmetic base" in accordance with the present invention is an unpigmented mixture of at least two silicone elastomers, at least one non-aqueous solvent which is compatible with the elastomer and at least one water insoluble structuring agent which is compatible with that solvent. More preferably, the cosmetic base includes a plurality of nonemulsifying silicone elastomers that are distinct. One preferably can form a sustainable gel with a compatible solvent. This is referred to herein as a "first elastomer." This is also referred to herein as being "gellable." A second elastomer generally cannot produce a sustainable gel with that same solvent. This is the "second elastomer." This is "nonsustainable." More than one first elastomer and/or more than one second elastomer may be used to make formulations in accordance with the present invention.

In another embodiment, a cosmetic base also includes an emollient, often one that is a silicone compatible oil.

A cosmetic base in accordance with the present invention can include additional ingredients or additives normally found in the cosmetic and personal care products as well as pharmaceutically active agents, most notably topically active or transdermally deliverable pharmaceuticals. These additives can include, without limitation fillers, film formers, emulsifiers, UV filters, topical antibiotics or steroids and the like. Cosmetic bases may be applied to skin and hair and may serve as cosmetics where the use of coloration is undesired or not required.

A "cosmetic composition" in accordance with the present invention includes a cosmetic base as defined herein and at least one pigment. "Pigment," as used in the context of the present invention refers generically to any coloring agent which may be used in coloring, permanently, semi-permanently or temporarily skin or hair. The term pigment as used herein includes, without limitation, traditional pigments, colors and dyes as well as materials which can be used in combination to produce color such as hydrogen peroxide when reacted with the appropriate dye or dye precursor.

The formulations in accordance with the present invention are often anhydrous. "Anhydrous" (used synonymously with "non-aqueous") in accordance with the present invention means that the formulation, be it a cosmetic base or cosmetic composition, exists substantially in the absence of water. While formulations which are completely water free or which have only trace amounts of water are most desired, the term is meant to encompass total water contents of up to about 5% by weight. Water content is to be minimized, however, wherever possible.

The present invention uses two different types of silicone elastomers in the formulations, one of which is the "first elastomer" or "first silicone elastomer" and the second is the "second elastomer" or "second silicone elastomer." Not all silicone elastomers are preferred for use in accordance with the present invention. Generally, all of the silicone elastomers contemplated should be nonemulsifying. However, some emulsifying elastomers may be used, particularly in lesser amounts, as additives. If present at all, such emulsifying elastomers should be used in an amount of less than 2% w/w, more preferably 1% or less w/w. A "nonemulsifying elastomer" is generally recognized as one which is a polyorganosiloxane which does not include hydrophilic groups and in particular polyoxyethylene or (poly(oxyethylene/oxypropylene)) groups.

The silicone elastomers useful in accordance with the present invention as first elastomers must be "gellable" or capable of forming a gel when mixed with the appropriate solvent and/or additional gelling agent(s). Some silicone elastomers useful as first elastomers in accordance with the present invention are sold commercially in a pre-gelled form. Others, exist as particulate or powder. Either may be used so long as the resulting material is gelled and/or capable of being gelled.

The first elastomer in accordance with another aspect of the present invention is a material that will swell in the presence of a solvent such as D5 (cyclopentasiloxane) and form a stable gel that is also preferably pilling in nature and/or sustainable. A "sustainable" gel in accordance with the present invention means that one can make a ball or shape out of it and manipulate it manually. It may ooze or spread, but its viscosity is preferably such that it will remain as a cohesive mass. Something that cannot do this is "non-sustainable." Preferred first elastomers may be manipulated manually, such as rolling it in their hands without it breaking apart or adhering to any significant degree for at least some period of time ("pilling"). Something that cannot do this is "non-pilling." Generally the resulting gels are not free flowing, although they can be pumped or forced to flow and to fill a desired space such as the lumen of a package. An example of the first elastomer is Dow Corning 9040 Silicone elastomer blend which is a cyclopentasiloxane (and) dimethicone crosspolymer. Dimethicone crosspolymers in general are examples of suitable first elastomers, preferably pregelled using D5 or a like solvent.

As compared with elastomers useful as second elastomers, these first elastomer materials tend to be somewhat tacky in feel when rubbed into the skin. They also often exhibit a balling or pilling, like a sweater, when rubbed onto the skin.

The first elastomers may, in addition or instead, be characterized by being a cross-linked silicone elastomer and blends thereof and they are generally not considered spherical. They are often considered to be made from relatively high molecular weight silicone elastomers. These include those described in U.S. Pat. Nos. 5,599,533 and 6,027,738, the texts of which are hereby incorporated by reference. Other examples of first elastomers in accordance with the present invention are any which fulfill the characteristics noted previously as GE's Velvesil, GE's SFE 839 and Shin-Etsu's KSG 6, 15, 16, 17, and 18.

The amount of the at least one first silicone elastomer present in a formulation must be an amount that is effective to produce a mousse base having the properties desired. Desirably, the effective amount is sufficient to, when taken in combination with the other ingredients, provide a stable formulation (cosmetic composition) whose Hardness (penetration by measurement of force) ranges from about 10 to about 50 g, more preferably from about 10 to about 40 g, even more preferably between about 10 and about 30 g and most preferably from about 12 g to about 25 g.

Generally, however, the amount of first elastomer used in accordance with the present invention ranges from about between about 0.1 and about 40% by weight of dry elastomer based on the weight of the formulation. The phrase "by weight of dry elastomer" means the amount of elastomer used in dry, particulate or powder form or the amount of elastomer in the gel if in gel form. As previously noted, first elastomers can be provided in a particulate form or, often, mixed with solvent and/or pre-gelled. The amount of elastomer by weight of dry elastomer is simply the weight of material used assuming it was in a dry powder. However, when used in a pre-gelled form, it is the weight of dry elastomer used in the gel, liquid or other form minus any solvent or other ingredients. More preferably, the amount of gellable, nonemulsifying first silicone elastomer ranges from between about 1 and about 20% by weight and even more preferably, between about 3 and about 15% by weight.

These weight percentages represent the total amount of first elastomer in the cosmetic base or cosmetic composition. Even if a plurality (two or more) of such first elastomers are used in combination, as is the case with several preferred embodiments, the total amount will be unchanged. This also holds true for the second elastomer. In such an instance, where a plurality of first elastomers are used, any proportion of two or more elastomers may be used.

The at least one second elastomer is also preferably a nonemulsifying silicone elastomer. However, the second elastomer need not necessarily be gellable. Gels produced from the second elastomer are not generally sustainable ("non-sustainable") as described in connection with the first elastomer. The second elastomer must be swellable in a silicone solvent such as D5 and include, relative to the first elastomer, a more spongy or rubber-like feel. Generally, upon the application of pressure, even when sufficient solvent is present, such as when manipulated by one's fingers over the palm of one's hand, spreading is efficient, silky and smooth. Often, it is accompanied with a generally "floating" or "gliding" sensation that occurs without balling up or pilling.

The floating sensation is somewhat difficult to articulate in words, although those of ordinary skill in the art would clearly appreciate it. While the material is being spread, it does not feel like the area of contact is as large as the amount of material actually being applied. A somewhat analogous sensation comes from contact with small ball bearings in one's palm. Looking at the total number of balls, a considerable area is covered. However, because of their generally spherical shape, only a relatively small percentage of the surface area of the palm underneath is actually directly in contact with a ball bearing. This sensation can be exemplified by adding sufficient D5 solvent so that dimethicone/vinyl dimethicone crosspolymer material swells but no free solvent is allowed to pool or puddle and the resulting material is not sustainable. Preferred second elastomers in accordance with the present invention include Dow Corning DC 9506 Silicone elastomer powder. It is preferably used as a powder. DC9506 is a dimethicone/vinyldimethicone crosspolymer which is generally spherical. Another preferred second elastomer is Dow Corning 9701 cosmetic powder, which is a spherical silicone elastomer powder coated with silica (INCI name dimethicone/vinyl dimethicone cross-polymer (and) silica). See also U.S. Pat. Nos. 5,945,471 and 5,492,945 and Japanese Application Nos. JP 2001114623, JP 9315936, JP 10130120 and JP 9071509. It is not required that second elastomers be spherical, but those which are and which have properties similar to DC 9506 and DC 9701 in terms of oil and sebum adsorption, silky, floating feel, with a similar "bounce" or "cushion" may be used, so long as they are compatible. Preferably, the second elastomer is used in the form of a powder, preferably one with an aerated bulk density of about 0.18 or lower.

The amount of second elastomer useful in accordance with the present invention covers the same general range as those previously identified for the first elastomer. Preferably an effective amount is used that being an amount, when taken in combination with the other ingredients, will produce a stable formulation whose Hardness (penetration by measurement of force) ranges from about 10 to about 50 g, more preferably from about 10 to about 40 g, even more preferably between about 10 and about 30 g and most preferably from about 12 g to about 25 g.

More preferably, the amount of the second elastomer ranges from between about 0.10 to about 40% by weight of dry elastomer based on the weight of the formulation and more preferably between about 1 and about 20% by weight thereof. Most preferably between about 3 and about 15% by weight may be used. These weight percentages represent the total amount of the second silicone elastomer in a cosmetic base or cosmetic composition. Even if a plurality (two or more) of such second silicone elastomers are used in combination, the total amount will be unchanged.

It has also been observed that advantages can be obtained by the use of a first elastomer, which is added to the formulation as a pregelled material and a second elastomer, which is either in the form of a dry powder, a wet powder, or which is dissolved or dispersed to some degree in a solvent, but which is not in a stable, sustainable gel. Without wishing to be bound by any particular theory of operation, it is believed that by the use of disparate forms of elastomer, as well as different elastomers in certain embodiments, it is possible to obtain a more non-homogeneous formulation, somewhat analogous to the development of curds during cheese making. This has been found to be an advantage in certain embodiments. It has also been found that when significant amount of high-shear mixing is used in an attempt to produce some formulations in accordance with the present invention, while a smooth velvety texture may be obtained, it is not always possible to obtain the appropriate look, feel, and consistency of a mousse as is desired. The curds have been destroyed or minimized. Therefore, the degree of mixing should be carefully managed.

The areas of non-homogeneity or curds can be thought of as agglomerates of slightly different viscosity, texture and/or the like which, when applied as part of the formulation, add by virtue of their ability to be rolled and manipulated, as well as their ability to rupture, a particularly unique tactile sensation. More than one different type of elastomer and more than one form of elastomer may be desirable.

Silicone elastomers useful in accordance with the invention as first or second elastomers, depending upon their individual properties include, without limitation, compounds generally known as polyorganosiloxanes. These may be made of cross-linked elastomeric polyorganosiloxanes described in application EP-A-0,295,886, the disclosure of which is incorporated herein by reference. According to that application, they are obtained by addition reaction and cross-linking, in the presence of a platinum-type catalyst, of at least:

(a) a polyorganosiloxane having at least two $C_2$ to $C_6$ lower alkenyl groups per molecule; and (b) a polyorganosiloxane having at least two hydrogen atoms linked to a silicon atom per molecule. It is also possible to use polyorganosiloxanes described in U.S. Pat. No. 5,266,321, the disclosure of which is incorporated by reference herein. According to that patent, they are chosen in particular from:

i) polyorganosiloxanes comprising $R_2SiO$ and $RSiO_{1.5}$ units and optionally $R_3SiO_{0.5}$ and/or $SiO_2$ units in which the radicals R, independently of each other, are chosen from a hydrogen, an alkyl such as methyl, ethyl or propyl, an aryl such as phenyl or tolyl, an unsaturated aliphatic group such as vinyl, the weight ratio of the units $R_2SiO$ to the units $RSiO_{1.5}$ ranging from 1/1 to 30/1;

ii) polyorganosiloxanes which are insoluble and swellable in silicone oil, obtained by addition of an polyorganohydrogenosiloxane (1) and of a polyorganosiloxane (2) having unsaturated aliphatic groups such that the amount of hydrogen or of unsaturated aliphatic groups in (1) and (2) respectively ranges from 1 to 20 mol % when the polyorganosiloxane is non-cyclic and from 1 to 50 mol % when the polyorganosiloxane is cyclic.

As examples of polyorganosiloxanes which can be used according to the invention, mention may be made of those sold or made under the names KSG6 from Shin-Etsu, Trefil E-505C or Trefil E-506C from Dow-Corning (now known as DC 9506), Gransil from Grant Industries (SR-CYC, SR DMF10, SR-DC556) or those marketed in the form of pre-constituted gels (KSG15, KSG17, KSG16, and KSG18 from Shin-Etsu, Gransil SR 5CYC gel, Gransil SR DMF 10 gel, Gransil SR DC556 gel, SF 1204 and JK 113 from General Electric. A mixture of these commercial products may also be used.

Other nonemulsifying silicone elastomers which can be used include GE's Velvesil which is described in U.S. Pat. No. 6,444,745, and EP1164172 A1; GE's SFE 839, which is described in U.S. Pat. No. 5,760,116 and EP0827983 A2; Dow Corning's DC 9506, which is described in EP0381166B1, and U.S. Pat. No. 4,980,167; and Dow Corning's DC9040 which is described in U.S. Pat. No. 5,654,362.

Still other materials useful herein as silicone elastomers, particularly elastomer particles, are those nonemulsifying polyorganosiloxanes described in: Tokkai2000-038314, Tokkai2000-038316, Tokkai2000-038317, Tokkai2000-038321, Tokkaihei9-020631, Tokkaihei10-120903, Tokkaihei11-335228, Tokkaihei11-335242, Tokkaihei11-335254, Tokkai2000-086429, Tokkai2000-086427, Tokkai2000-086438, U.S. Pat. No. 5,538,793, WO02092047, WO0203951, WO0203950, WO0203935, WO0203932, EP0958804, EP0958085, EP1062944, EP1062959, EP1213011, EP1213316, EP1095959, U.S. Pat. Nos. 6,479,686, 6,475,500, U.S. application Publication No. 2002/0131947, U.S. application publication No. 2002/0159964, U.S. application Publication No. 2001/0014312, U.S. application Publication No. 2002/0114771, U.S. Pat. No. 6,399,081, U.S. application Publication No. 2002/0058053, U.S. application Publication No. 2002/0081323, U.S. application Publication No. 2002/0102225, and U.S. application Publication No. 2002/0141958, the recitations of elastomers of which are all incorporated herein by reference. Also included are the nonemulsifying silicone elastomers described in U.S. patent application Publication No. US 2003/0165546A1, and specifically, paragraph nos. 109 and 110 which is also hereby incorporated by reference. Also useful as first or second elastomers are the elastomers listed in U.S. Pat. No. 6,475,500 to Vatter et al., issued Nov. 5, 2002, the elastomers from which are hereby incorporated by reference. Generally the elastomers therein listed as Spherical are likely to be second elastomers in the cosmetic bases and cosmetic compositions of the present invention.

A cosmetic base in accordance with the present invention also includes at least one non-aqueous solvent, most preferably one based on silicone. This solvent is generally anhydrous as previously defined, and is usually volatile.

The amount of solvent used in accordance with the present invention must be sufficient to completely solubilize, suspended or disperse the necessary ingredients. The amount of solvent used may also depend on whether or not the solvent is volatile and what other ingredients are intended as well as the final hardness, viscosity, specific gravity or other desirable properties of the cosmetic base or composition. Generally, the balance of the formulation will be solvent, however, the amount of solvent can range as high as 95% by weight. And while it is difficult to identify a minimum amount of solvent as it will depend on a number of factors including the number and amount of other ingredients contained within the formulation, generally at least about 20% of each formulation will be solvent by weight. Preferably the amount of solvent ranges from about 30 to about 80% by weight.

The solvent can also be part of a co-solvent system, in which case, hydrocarbon based co-solvents, such as for examples isododecane may be used. However, the amount of hydrocarbon co-solvent used will generally not exceed about 20%, based on the total amount of solvent used. This assumes however that the solvent system includes a silicone based solvent, which need not be the case. Preferably, the amount of such hydrocarbon solvents, if used at all, will be less than about 10% of the overall solvents used in the system. Examples of silicone containing solvents useful in accordance with the present invention include the volatile silicone oils of linear or cyclic silicones having a flash point of at least about 40° C., such as linear or cyclic polydimethylsiloxanes.

Non-limiting examples of such volatile oils are given in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

Other non-limiting examples of silicone containing volatile oils that may be used as solvents in according to the invention are linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96 A of 6 cSt viscosity, a commercial product from Shin Etsu having a flash point of 94° C. Other volatile silicones are described and/or claimed in: WO03/042221, U.S. Pats. No. 5,919,467, 6,350,440, 5,925,338, 5,759,529, 6,235,292, 5,750,098, 5,830,527, 6,184,277, WO95/25499, WO95/25503, U.S. Pat. Nos. 6,177,091, 5,972,318, 3,418,353, JP03-264510 (publication on Nov. 25, 1991), the disclosures of which are hereby incorporated by reference.

Other volatile oils usable in this invention, particularly as co-solvents, may include volatile hydrocarbon oils.

Examples of hydrocarbon oil based co-solvents which may be useful in accordance in the present invention include non-silicone volatile oils may be selected from the group of volatile hydrocarbon oils, volatile esters and volatile ethers. This includes, but is not limited to, volatile hydrocarbons, such as isododecane and isohexadecane, isoparaffins, $C_8$-$C_{16}$ alkanes such as isoalkanes, isohexyl or isodecyl neopentanoates isodecane, ISOPAR, PERMETHYL and the $C_8$-$C_{16}$ branched esters such as isohexyl neopentanoate and their mixtures.

Non-limiting examples of such volatile hydrocarbon oils are given in Table 2 below.

TABLE 2

| Compound | Flash Point (° C.) |
| --- | --- |
| Isododecane | 43 |
| Isohexadecane | 102 |
| Isodecyl Neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

These oils may be optionally substituted with pendant or terminal alkyl or alkoxy groups, or a mixture of these oils.

The formulations of the present invention also include a water insoluble structuring agent. This structuring agent must be compatible with the solvent and elastomers used. Generally, waxes such as paraffin, mineral based waxes and carnauba waxes are not sufficiently compatible with silicone based solvents and elastomers and therefore, they are generally inappropriate or less desirable. However, it is possible to modify the solubility characteristics of the solvents by selection of an appropriate hydrocarbon based solvent or co-solvent and some otherwise incompatible waxes may be compatibilized sufficiently in this manner. Preferred, however, are structuring agents which are completely compatible with the formulation based solely on silicone based solvents.

Compatibility in accordance with the present invention can be determined by those of skill in the art by observing whether or not the blend of solvent and compatibilizer promotes syneresis or sweating of solvent from the compatibilizer. An effective amount of water insoluble structuring agent is contemplated in accordance with the present invention. An effective amount of this material is one that is compatible with the other ingredients within the base to form a mousse formulation having the desired properties. In general, however, the amount of insoluble structuring agent used in accordance with the present invention ranges from about 0.1 to about 30% by weight based on the cosmetic formulation, more preferably between about 0.1 and about 20% by weight, even more preferably 0.5 and about 15% by weight and most preferably between about 1 and about 6% by weight of the base.

Particularly preferred structuring agents in accordance with the present invention are those which are compatible with a silicone based solvent and the elastomers used in accordance with the present invention. Most preferred are those which have melting points, of between about 45 and about 95° C. Non-limiting examples of structuring agents include waxes of natural origin, to the extent that they are compatible with the solvents and elastomers of the invention, such as beeswax, modified beeswax, carnauba wax, candelilla wax, jojoba wax, ouricury wax, Japan wax, cork fiber wax, sugar cane wax, non-linear paraffin waxes, lignite wax, microcrystalline waxes, lanolin wax, montan wax and ozokerites, hydrogenated oils such as hydrogenated jojoba oil, jojoba esters, waxes obtained by Fischer-Tropsch synthesis, fatty acid esters, fatty acid glycerides, and silicone waxes. Most preferred of these are the silicone derivatized waxes such as silicone modified beeswax. Linear hydrocarbon waxes which may be used, to the extent that they are compatible in the cosmetic formulations of the present invention include polyethylene waxes such as Polyethylene 400 and Polyethylene 500, which are commercially available from New Phase Technologies, linear paraffin waxes such as paraffin S&P 206, S&P 173, and S&P 434, which are available from Strahl & Pitsch, and long-chain linear alcohols such as products comprising blends of long-chain linear alcohols and polyethylene such as Performacol 425 ($C_{20}$-$C_{40}$ alcohols and polyethylene) and Performacol 550 ($C_{30}$-$C_{50}$ alcohols and polyethylene), which are commercially available from New Phase Technologies.

The formulations of the present invention, both cosmetic bases and cosmetic compositions, can also be described by certain advantageous rheological properties.

The complex modulus or $G^*(\omega)$ can be measured by dynamic oscillation. The ratio of storage modulus or elastic modulus ($G'(\omega)$) divided by loss modulus ($G''(\omega)$) is a measure of same. These can be measured at various frequencies. However, for use herein, measurement can be taken at either 0.1 rad/s or 100 rad/s or both. Complex modulus can be measured using a controlled-stress rheometer: Model AR2000 (TA instrument) with a parallel plate geometry of a diameter of 40 millimeters. The gap is set at 1 millimeter. The rheological measurements are performed at 25° C. The measurement of dynamic oscillation is performed in a linear viscoelastic regime at an applied stress of 1.0 Pascal. From this experiment, the storage modulus and the loss modulus are obtained as a function of frequency from ($\phi$)=100 rad/s to 0.1 rad/s.

The real or in-phase component of the complex dynamic viscosity $\eta'(\omega)$ is related to the loss modulus $G''(\omega)$ by the formula $\eta'(\omega)=G''(\omega))/\omega$. See Viscoelastic Properties of Polymers, John D. Ferry, John Wiley & Sons, third edition, 1980, or Chapter 6, page 242 in Polymer Viscoelasticity: Stress and Strain in Practice, Evaristo Riande et al, Marcel Decker, Inc., 2000.

When frequency is 100 rad/sec, the relationship G'/G" can range from about 1 to about 100. In another embodiment, it can range from about 1.2 to about 50, and in another embodiment, from about 1.3 to about 25. In another embodiment, it can range from about 1.5 to about 7. When measured at a frequency of 0.1 rad/sec, the ratios are about 0.1 to about 100, about 1 to about 50, about 2.5 to about 25, and about 3 to about 4, respectively. In a preferred embodiment, the formulations of the invention will meet both ranges at 100 and 0.1 rad/s as described earlier herein.

Dynamic viscosity ranges in accordance with one embodiment of the present invention can range from about $1\times10^1$ to about $9\times10^6$ Pa·s. In another embodiment, dynamic viscosity can range from about $1\times10^2$ to about $5\times10^6$ Pa·s. and in yet another embodiment from about $1\times10^3$ to about $1\times10^6$ Pa·s. In still another embodiment, dynamic viscosity can range from about $2\times10^3$ to about $1\times10^5$ Pa·s.

In another embodiment, G'/G" at 100 rad/s is from about 1 to about 100, G'/G" at 0.1 rad/s is from about 0.1 to about 100 and dynamic viscosity is about $1\times10^1$ to about $9\times10^6$ Pa·s. In another embodiment, G'/G" at 100 rad/s is from about 1.2 to about 50, G'/G" at 0.1 rad/s is from about 1 to about 50 and dynamic viscosity is about $1\times10^2$ to about $5\times10^6$ Pa·s. In yet another embodiment, G'/G" at 100 rad/s is from about 1.3 to about 25, G'/G" at 0.1 rad/s is from about 2.5 to about 25 and dynamic viscosity is about $1\times10^3$ to about $1\times10^6$ Pa·s. In still another embodiment, G'/G" at 100 rad/s is from about 1.5 to about 7, G'/G" at 0.1 rad/s is from about 3 to about 4 and dynamic viscosity is about $2\times10^3$ to about $1\times10^5$ Pa·s. It is also preferred that these formulations also have the hardness discussed elsewhere herein.

Another useful component of cosmetic bases in accordance with the present invention, and one which is often found in such bases, is an emollient. Emollients help in retaining the solvent and improve the feel and/or performance of the formulations in accordance with the present invention. These emollients are preferably silicone compatible oils that mimic or are compatible with a lipophilic content generally found within skin or hair. A preferred emollient is squalane. However, many traditional silicone compatible oils may be used. Useful emollients include, but are not limited to fatty bodies liquid at ambient temperature, such as esters, mineral oils, animal oils, vegetable oils, synthetic oils, and silicone oils. Examples of useful esters include, but are not limited to, isononyl isononanoate, octyl palmitate, cetyl lactate, pentaerythrityl tetraoctanoate, tridecyl octanoate, tridecyl behenate, isopropyl jojobate and jojoba alcohols, butyloctyl salicylate, polyglyceryl-3 diisostearate, tridecyl trimellitate, tridecyl stearate, and neopentylglycol dicaprylate/dicaprate. In one embodiment of the invention, the esters are chosen from isononyl isononanoate, a light ester which adds to the initial feel of the inventive composition on the skin, and pentaerythrityl tetraoctanoate, an ester which helps to cushion after the makeup is blended into the skin. Examples of useful oils include, but are not limited to, petrolatum oil, liquid lanolin, arara oil, sesame oil, macadamia oil, jojoba oil, silicone oils such as phenyl trimethicone and dimethicone, and synthetic triglycerides such as capric caprylic triglyceride and hydrogenated cocoglycerides.

The silicone compatible organic oil which may be used as emollients also include esters, hydrocarbon oils, or an animal, vegetable, or mineral oils. The term compatible means that the organic oil is soluble or dispersible in the silicone mixture to form a stable solution or dispersion. Esters include mono-, di-, and triesters. The composition may comprise one or more esters selected from the group, or mixtures thereof. Preferably the composition contains a mixture of di- and triesters. Monoesters are defined as esters formed by the reaction of a monocarboxylic acid having the formula R—COOH, wherein R is a straight or branched chain saturated or unsaturated alkyl having 2 to 30 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups, and in one preferred embodiment of the invention the acid is an alpha hydroxy acid. Either one or both of the acid or alcohol may be a fatty acid or alcohol, i.e. may have from about 6 to 22 carbon atoms. Examples of monoester oils that may be used in the compositions of the invention include hexyl decyl benzoate, hexyl laurate, hexadecyl isostearate, hexyldecyl laurate, hexyldecyl octanoate, hexyldecyl oleate, hexyldecyl palmitate, hexyldecyl stearate, hexyldodecyl salicylate, hexyl isostearate, butyl acetate, butyl isostearate, butyl oleate, butyl octyl oleate, cetyl palmitate, ceyl octanoate, cetyl laurate, cetyl lactate, cetyl isononanoate, cetyl stearate, stearyl lactate, stearyl octanoate, stearyl heptanoate, stearyl stearate, and so on. It is understood that in the above nomenclature, the first term indicates the alcohol and the second term indicates the acid in the reaction, i.e. stearyl octanoate is the reaction product of stearyl alcohol and octanoic acid. Preferred is monoester which is the reaction product of an aliphatic $C_{2-8}$ alcohol and a $C_{14-22}$ fatty acid, more particularly, the reaction product of a hexyl alcohol and lauric acid, also referred to as hexyl laurate.

Suitable diesters that may be used in the compositions of the invention are the reaction product of a dicarboxylic acid and an aliphatic or aromatic alcohol. The dicarboxylic acid may contain from 2 to 30 carbon atoms, and may be in the straight or branched chain, saturated or unsaturated form. The dicarboxylic acid may be substituted with one or more hydroxyl group. The aliphatic or aromatic alcohol may also contain 2 to 30 carbon atoms, and may be in the straight or branched chain, saturated, or unsaturated form. The aliphatic or aromatic alcohol may be substituted with one or more substituents such as hydroxyl. Preferably, one or more of the acid or alcohol is a fatty acid or alcohol, i.e. contains 14-22 carbon atoms. The dicarboxylic acid may also be an alpha hydroxy acid. Examples of diester oils that may be used in the compositions of the invention include diisostearyl malate (the reaction product of isostearic alcohol and malic acid), neopentyl glycol dioctanoate (the reaction product of neopentyl glycol and 2-ethyl hexanoic acid), dibutyl sebacate (reaction product of butyl alcohol and sebacic acid), di-$C_{12-13}$ alkyl malate (reaction product of $C_{12-13}$ alcohol and malic acid), dicetearyl dimer dilinoleate (reaction product of cetearyl alcohol and adipic acid), dicetyl adipate (reaction product of cetyl alcohol and adipic acid), diisocetyl adipate (reaction product of hexadecyl alcohol and adipic acid), diisononyl adipate (reaction product of isononyl alcohol and adipic acid), diisostearyl dimer dilinoleate (reaction product of isostearyl alcohol and dilinoleic acid), disostearyl fumarate (reaction product of isostearyl alcohol and fumaric acid), and so on.

Suitable triesters comprise the reaction product of a tricarboxylic acid and an aliphatic or aromatic alcohol. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 14 to 22 carbon atoms. Examples of triesters include triarachidin (reaction product of glycerin and arachidic acid), tributyl citrate (reaction product of butyl alcohol and citric acid), tri $C_{12-13}$ alkyl citrate (reaction product of $C_{12-13}$ alcohol and citric acid), tricaprylin (reaction product of glycerin and caprylic acid), tricaprylyl citrate (reaction product of capryl alcohol and citric acid), tridecyl behenate (reaction product of tridecyl alcohol and behenic acid), trioctyldodecyl citrate (reaction product of octyldodecyl alcohol and citric acid), tridecyl behenate (reaction product of tridecyl alcohol and behenic acid), tridecyl cocoate (reaction product of tridecyl alcohol and coconut acid), tridecyl isononanoate (reaction product of tridecyl alcohol and isononanoate), and so on. Preferred is a triester which is the reaction product of an alpha hydroxy acid and a guerbet alcohol having 6 to 30 carbon atoms, in particular the reaction product of citric acid and octyldodecyl alcohol, referred to as trioctyldodecyl citrate.

Suitable hydrocarbon oils used in the compositions of the invention may be volatile or nonvolatile. The term volatile means that the oil has a measurable vapor pressure, or a vapor pressure of at least 2 mm. of mercury at 20° C. The term nonvolatile means that the oil has a vapor pressure of less than 2 mm. of mercury at 20°. Examples of volatile hydrocarbon oils that may be used in the compositions of the invention include various straight or branched chain paraffinic hydrocarbons having 5 to 20 carbon atoms, more preferably 8-20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70-225, preferably 160 to 190 and a boiling point range of 30 to 320, preferably 60-260° C., and a viscosity of less than 10 cs. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99 A. Another $C_{12}$ isoparaffin (isododecane) is distributed by Presperse under the tradename Permethyl 99 A. Various $C_{16}$ isoparaffins commercially available, such as isohexadecane (having the tradename Permethyl R), are also suitable.

Suitable nonvolatile hydrocarbon oils include isoparaffins and olefins having greater than 20 carbon atoms. Examples of such hydrocarbon oils include $C_{24-28}$ olefins, $C_{30-45}$ olefins, $C_{20-40}$ isoparaffins, hydrogenated polyisobutene, mineral oil, pentahydrosqualene, squalene, squalane, and mixtures thereof Also suitable for use in the composition is lanolin oil or derivatives thereof such as hydroxylated lanolin, isobutylated lanolin oil, acetylated lanolin, acetylated lanolin alcohol, and so on.

Another useful emollient is an oleosoluble synthetic polymer whose use in cosmetic compositions is known. Representative oleosoluble synthetic polymers include polyvinylpyrrolidone/hexadecene or PVP/eicosene copolymers, such as products sold by GAF Corp. under the tradenames GANEX V-216 and GANEX V-220. Other useful skin conditioning emollients are listed in the International Cosmetic Ingredient Dictionary and Handbook, 7th Edition, Vol. 2, pp. 1656-1661 (1997).

When used, the amount of emollient should range from between about 0.5 to about 80% based on the weight of the total cosmetic base or composition. In an alternate embodiment, it should range from between about 1 to about 40%, more preferably from between about 1 to about 30%, even more preferably about 1 to about 20%, and most preferably from between about 1 to about 10%.

A cosmetic base in accordance with the present invention can be produced by placing all of the required ingredients into a single reactor and blending for a period of time of between about 15 to about 60 minutes, using for example, a non high-shear mixer. Care should be taken not to overblend as this will prevent the structuring of the base into a formulation such as a mousse.

A cosmetic composition in accordance with the present invention is similar to a cosmetic base. Indeed, it includes a cosmetic base as previously described. However, in addition, a cosmetic composition includes a pigment or other form of coloring material (collectively pigments). Pigments generally should not be added directly to a pre-formed based. The degree of mixing required to provide a homogenous distribution of the pigment once the base has been formed is often sufficient to impart undesirable properties in the resulting formulation.

The amount of pigment used in accordance with the present invention will depend upon a number of factors including the type of pigment or coloring material, the degree of coloration desired, the use of the cosmetic (for example, blush, eye shadow or foundation) and the composition of the base. However, pigment content can be as high as about 60% by weight of the composition, more preferably, up to about 25% w/w of the cosmetic formulation. Pigments may be selected from pigments, coloring agents, dyes, such as liposoluble dyes, nacreous pigments, and pearling agents. The at least one pigment may be chosen, for example, in order to obtain emulsions which give good coverage. The pigment may also reduce any sticky feel of the product, if any.

Representative liposoluble dyes which may be used according to the present invention include Sudan Red, DC Red 17, DC Green 6, .beta.-carotene, soybean oil, Sudan Brown, DC Yellow 11, DC Violet 2, DC Orange 5, annatto, and quinoline yellow. The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The pigments which may be used according to the present invention may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, manganese violet, ultramarine blue, chromium hydrate, and ferric blue. Representative examples of organic pigments include carbon black, pigments of D & C type, and lakes based on cochineal carmine, barium, strontium, calcium, and aluminum. The pigment may be chosen from encapsulated pigments. As used herein, "encapsulated pigments" refer to pigments which are encapsulated within at least one polymer. The capsule may release some of its contents, i.e., the enclosed pigment and dispersing solvent, if present, when pressure is applied to the emulsion comprising such encapsulated pigments. Alternatively, the encapsulant may be dissolvable with heat or time and/or may be robust and resist breakage.

In an embodiment in accordance with the present invention, a cosmetically acceptable film former may be added to the cosmetic base or cosmetic composition. Film formers, when properly selected and properly used can impart substantivity and excellent wear.

Not all film formers are desirable in accordance with the present invention. Indeed, where anhydrous formulation with only trace amounts of water, less than 1%, are achieved, the film formers could be silicone based resins such as so called MK and MQ resins, silicones acrylates, vinyl silicones, and other organsiloxane resins. Generally, water soluble film formers such as acrylics and latexes are undesirable. Materials such as latexes, may possibly be used when the amount of water in the formulation is relatively high, e.g., greater than about 1% by weight. However, even in these circumstances, an emulsifier is generally required.

The preferred film formers in accordance with the present invention generally will not require any sort of emulsifier be used in order to compatibilize them with the cosmetic compositions and cosmetic bases of the present invention. This does not mean, however, that small amounts of emulsifier may not be used in the formulation.

Film formers in accordance with the present invention are generally used in amounts ranging from between about 0.1 to about 10% by weight, more preferably about 0.1 to about 5% by weight, more preferably about 0.1 to about 4% by weight based on the total weight of the cosmetic base or cosmetic composition as appropriate. When emulsifier are used, they are generally not used to help emulsify the film former, but instead to help disperse pigments. Perhaps the term "dispersing agent" is more appropriate. Emulsifiers when used at all, should be used sparingly and in particular, in an amount between about 0.1 to about 5% maximum.

Film formers that are compatible in the present invention, without the need of an emulsifier include, without limitation, those that contain repeating monofunctional or $R_3SiO_{1/2}$ (M units) and quadrafunctional or $SiO_2$ (Q units), otherwise known as "MQ" resins as described in U.S. Pat. No. 5,330,747, which descriptions are incorporated herein by reference. Examples of highly preferred organosiloxane resins are those in which the ratio of "M" to "Q" functional units is about 0.5 and the value of n is 1.5, non limiting examples of which are commercially available from Wacker Silicones Corporation of Adrian, MI (e.g., Wacker 803 and 804) and the General Electric Company (e.g., G. E. SR 1000 or 1170-002). Other suitable organosiloxane resins includes functionalized silicone resins such as silicone ester waxes comprising moieties of the general formula 1:

wherein R is an organic radical, R' is a carboxylic acid ester, "a" and "b" are integers independently either 1 or 2 wherein a+b equals 2 or 3. Other useful film formers include, without limitation, multiaklyl siloxysilicates such as trimethylsiloxysilicate sold by Wacker and designated Wacker-Belsil® TMS 803 (an "MQ" resin), silsesquioxanes such as polymethylsilsesquioxane and alkylphenylsilsesquioxane, both sold by Wacker designated Wacker-Belsil® PMS MK and SPR45 respectively, cyclopentasiloxane and dimethicone/vinyltrimethylsiloxysilicate crosspolymer sold by Wacker and designated Wacker-Belsil® RG100 and cyclopentasiloxane and stearyldimethiconesilicate crosspolymer sold by Wacker and designated Wacker-Belsil® RPG33.

Other suitable resins useful as film formers include U.S. patent application Publication No. US2002/0114773 which has a section on silicone resins, U.S. Pat. Nos. 5,676,938, 5,589,165, 6,589,517 and 5,015,469.

Note that a small amount, up to 5%, of silanol or alkoxy functionality may also be present in the resin structure as a result of processing. The organosiloxane resins are preferably solids at about 25° C. and have a molecular weight range of from about 1,000 to about 10,000 grams/mole. The resin is soluble in organic solvents such as toluene, xylene, isoparaffins, and cyclosiloxanes or the volatile carrier, indicating that the resin is not sufficiently crosslinked such that the resin is insoluble in the volatile carrier.

Emulsifiers or dispersing agents, useful in particular for dispersing pigment in this system include, without limitation, any which are compatible with the solvent and elastomers used and include those identified in U.S. patent application Publication 2003/0049212 published Mar. 13, 2003, paragraphs [0157] through [0179] are hereby incorporated by reference.

The formulations in accordance with the present invention can also use cosmetically acceptable additives which include fillers such as silica which can assist in providing a light and airy feel to the material. As used herein, the term "filler" means any particle that is solid at room temperature and atmospheric pressure, used alone or in combination, which does not react chemically with the various ingredients of the emulsion and which is insoluble in these ingredients, even when these ingredients are heated to a temperature above room temperature and, in particular, to their softening point or their melting point. In an embodiment, the at least one filler has a melting point at least greater than 170° C., for example, greater than 200° C. In an embodiment, the at least one filler may have an apparent diameter ranging from 0.01 microns to 150 microns, such as from 0.5 microns to 120 microns, for example from 1 microns to 80 microns. An apparent diameter corresponds to the diameter of the circle into which the elementary particle fits along its shortest dimension (thickness for leaflets). Further, the at least one filler may be absorbent, i.e., capable in particular of absorbing the oils of the composition and also the biological substances secreted by the skin, may be surface-treated, e.g., to make it lipophilic, and/or may be porous so as to absorb the sweat and/or sebum secreted by the skin.

The at least one filler may be chosen from inorganic and organic fillers, and may have any shape such as lamellar, spherical and/or oblong. Non-limiting examples of the at least one inert filler include talc, mica, silica, kaolin, polyamide powders (such as Nylon® powder, and such as the product sold by Atochem as Orgasol®), poly-.beta.-alanine powders, polyethylene powders, acrylic polymer powders (such as polymethyl methacrylate (PMMA) powder, for instance the product sold by Wacker as Covabead LH-85 (particle size 10-12 micrometers) and the acrylic acid copolymer powder sold by Dow Corning as Polytrap®), polytetrafluoroethylene (Teflon®) powders, lauroyllysine, boron nitride, silica, kaolin, starch, starch derivatives, hollow polymer microspheres (such as those hollow polymer microspheres formed from polyvinylidene chloride and acrylonitrile, for instance the product sold by Nobel Industrie as Expancel®), and polymerized silicone microspheres (such as those polymerized silicone microspheres sold by Toshiba as Tospearl®), precipitated calcium carbonate, magnesium carbonate and hydrocarbonate, hydroxyapatite, hollow silica microspheres (such as the product sold by Maprecos as Silica Beads®), glass microcapsules, ceramic microcapsules, and polyester particles.

In one particularly preferred aspect of the present invention, the resulting formulations, be they cosmetic bases or cosmetic compositions, will have a Hardness (penetration by measurement of force) which ranges from about 10 to about 50 g, more preferably from about 10 to about 40 g, even more preferably between about 10 and about 30 g and most preferably from about 12 g to about 25 g.

This can be measured using a stable microsystems texture analyzer model TA-XT2i. A 4 mm cylindrical probe is used with a trigger force of 2.0 g, a depth of 5 mm and a speed of 2.0 mm/second. The product should be filled in jars and conditioned at approximately 20° C. for 16-24 hours prior to conducting penetration testing.

Materials that may be used in these formulations may also include those discussed in WO 02/03935 A2 to Vatter et al. published Jan. 17, 2002, U.S. 2003/0161848 to Ferrari et al. published Aug. 28, 2003, U.S. 2003/0103918 to Jose et al. published Jun. 5, 2003, U.S. 2004/0018163 to Yu published Jan. 29, 2004, and U.S. Pat. No. 6,503,516 to Van Liew et al. published Jan. 7, 2003, to the extent they are noncumulative and consistent with the invention and the texts of which are attached and hereby incorporated by reference.

EXAMPLE 1

| USA/INCI name | Amount | Phase |
|---|---|---|
| DIMETHICONE/VINYL DIMETHICONE CROSSPOLYMER | 4.2 | A1 |
| DIMETHICONE CROSSPOLYMER (Gelled in D5) | 42* | A1 |
| VINYL DIMETHICONE/METHICONE SILSESQUIOXANE CROSSPOLYMER | 0.1 | A1 |
| SQUALANE | 7.5 | B1 |

-continued

| USA/INCI name | Amount | Phase |
|---|---|---|
| FILLERS | 0.2475 | B2 |
| PRESERVATIVES | 0.6 | B4 |
| COATED PIGMENTS | 13.0 | B4 |
| CYCLOPENTASILOXANE | 13.35 | A2 |
| DIMETHICONE | 9 | A2 |
| SILICONE RESIN | 1.2 | A3 |
| TOSPEARL | 1.2 | B2 |
| SILICA DIMETHYL SILYLATE | 0.5 | B3 |
| SILICA | 0.0525 | B2 |
| BISMUTH OXYCHLORIDE | 3 | B1 |
| POLYMETHYL METHACRYLATE | 1 | B2 |
| HYDROGENATED JOJOBA OIL | 2.6 | B5 |
| Total (including VI): | 99.55 | |

*weight of crosspolymer solids in the gel = 6.3%

To produce the mousse of the present invention, follow this general procedure.

Pigment Dispersion Phase
1. Pigment dispersion—Combine B1 and mix with spatula to obtain paste and then roller mill (~3-4 times). Check dispersion under microscope. Check shade characteristics.

Side Phase Beaker
2. Solubilize DIMETHICONE CROSSPOLYMER (of phase A1) in 50% of DIMETHICONE (of phase A2). Mix until uniform
3. Solubilize POLYMETHYLSILSESQUIOXANE (silicone resin) (of phase A3) in CYCLOPENTASILOXANE (of phase A2). Once completely solubilized, it should be transparent and free of white/translucent particulate.

Main Beaker
4. Combine pigment dispersion phase and the silicone oils from phase A2. Mix until uniform.
5. Add phase B2 powders and VINYL DIMETHICONE/METHICONE SILSESQUIOXANE CROSSPOLYMER (of phase A1). Mix until uniform.
6. Add phase B4. Mix thoroughly.
7. Add the first side phase solution (DIMETHICONE CROSSPOLYMER/DIMETHICONE) from step 2.
8. Add DIMETHICONE/VINYL DIMETHICONE CROSSPOLYMER (of phase A1). Mix until slightly homogeneous (not too homogeneous). Batch should be free of large lumps.
9. Add phase B5 and continue mixing. (Note: HYDROGENATED JOJOBA OIL will not melt completely until batch is heated to higher temperature).
10. Add second side phase solution (silicone resin/CYCLOPENTASILOXANE) from step 3.
11. Add B3 (SILICA DIMETHYL SILYLATE) and mix with high shear. The batch should start to thicken.
12. Heat batch to ~85 deg C. The batch will get thinner as the wax melts. Mix until completely melted.
13. Pour into containers (~75-80 deg C.).

EXAMPLE 2

Dissolve 1.2% w/w of polymethylsilsesquioxane (silicone resin) in 13.35% w/w cyclopentasiloxane (D5) as well as 0.05% w/w BHT. To this is added 7.5% w/w squalane, 0.4% w/w phenyl trimethicone and 0.6% w/w preservatives. This is all done with mixing.

Coated pigments in the amount of 13% w/w and fillers including mica, tospearl, silica, bismuth oxychloride, vinyl dimethicone/methicone silsesquioxane and polymethyl methacrylate (total 5.6% w/w) together are added to the mix above and ground.

Next, a mixture of dimethicone crosspolymer (6.3% w/w dry solids) in D5 (total weight 42% w/w) and dimethicone (9% w/w) is added. To this, 2.6% w/w hydrogenated jojoba oil is added and mixing continues. Next is added dimethicone/vinyl dimethicone crosspolymer (4.2% w/w) and silica dimethyl silylate (0.5% w/w) is added with mixing.

This is heated to 80-85 degrees C. and cooled to 70-75 degrees C. and filled into containers.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A cosmetic composition comprising:
a cosmetic base comprising an anhydrous mixture of an effective amount of at least one first non-emulsifying, gellable silicone elastomer ranging from about 0.1 to about 40% by weight of dry elastomer; an effective amount of at least one second non-emulsifying silicone elastomer wherein said second silicone elastomer is nonsustainable and nonpilling and present in an amount of about 0.1 to about 40% by weight of dry elastomer; at least one non-aqueous solvent; and an effective amount of at least one water insoluble structuring agent which is compatible with said solvent and which has a melting point of between about 45 and about 95° C.; and at least one pigment, wherein said composition has a hardness of from about 10 to about 50 gram-force, and wherein G'/G", measured at a frequency of 100 rad/s ranges from about 1 to about 100, and wherein the dynamic viscosity measured at a frequency of 0.1 rad/s is from about $1\times10^3$ to about $1\times10^6$ Pa·s., and wherein the composition is in the form of a mousse and wherein the cosmetic composition is free from any emulsifying silicone elastomer.

2. The cosmetic composition of claim 1, wherein said hardness is from about 10 to about 30 gram-force.

3. The cosmetic base of claim 2, wherein said hardness is from about 12 to about 25 gram-force.

4. The cosmetic composition of claim 1, wherein G'/G" measured at a frequency of 100 rad/s ranges from about 1.2 to about 50.

5. The cosmetic composition of claim 4, wherein G'/G" measured at a frequency of 100 rad/s ranges from about 1.3 to about 25.

6. The cosmetic composition of claim 5, wherein G'/G" measured at a frequency of 100 rad/s ranges from about 1.5 to about 7.

7. The cosmetic composition of claim 1, wherein G'/G" measured at a frequency of 0.1 rad/s ranges from about 0.1 to about 100.

8. The cosmetic composition of claim 7, wherein G'/G" measured at a frequency of 0.1 rad/s ranges from about 2.5 to about 25.

9. The cosmetic composition of claim 5, wherein G'/G" measured at a frequency of 0.1 rad/s ranges from about 2.5 to about 25.

10. The cosmetic composition of claim 6, wherein G'/G" measured at a frequency of 0.1 rad/s ranges from about 3.0 to about 4.0.

11. The cosmetic composition of claim 1, wherein the dynamic viscosity at a frequency of 0.1 rad/s is from about $2\times10^3$ to about $1\times10^5$ Pa·s.

12. A cosmetic composition comprising:
a cosmetic base comprising an anhydrous mixture of an effective amount of at least one first non-emulsifying, gellable silicone elastomer ranging from about 1 to about 20% by weight of dry elastomer; an effective amount of at least one second non-emulsifying silicone elastomer wherein said second silicone elastomer is nonsustainable and nonpilling and present in an amount of about 1 to about 20% by weight of dry elastomer; at least one non-aqueous solvent; and an effective amount of at least one water insoluble structuring agent which is compatible with said solvent and which has a melting point of between about 45 and about 95° C. present in an amount of at least about 0.5% by weight and at least one pigment in an amount of up to about 60% by weight, wherein G'/G", measured at a frequency of 0.1 rad/s ranges from about 0.1 to about 100 and dynamic viscosity ranges from about $1\times10^3$ to about $9\times10^6$ Pa·s, wherein the composition is in the form of a mousse and wherein the cosmetic composition is free from any emulsifying silicone elastomer.

13. The cosmetic composition of claim 12, wherein G'/G" measured at a frequency of 100 rad/s ranges from about 1 to about 100.

14. The cosmetic composition of claim 13, wherein G'/G" measured at a frequency of 100 rad/s ranges from about 1.3 to about 25.

15. The cosmetic composition of claim 14, wherein G'/G" measured at a frequency of 100 rad/s ranges from about 1.5 to about 7.

16. The cosmetic composition of claim 15, wherein G'/G" measured at a frequency of 0.1 rad/s ranges from about 2.5 to about 25.

17. The cosmetic composition of claim 1 or 12, wherein said at least first silicone elastomer is selected from the group consisting of dimethicone crosspolymer in cyclopentasiloxane, dimethicone/vinyl dimethicone crosspolymer in cyclopentasiloxane, simethicone, dimethicone/vinyl dimethicone crosspolymer in dimethicone, dimethicone/vinyl dimethicone crosspolymer in cyclotetrasiloxane, dimethicone/phenyl vinyl dimethicone crosspolymer in phenyl trimethicone, and C30-45 alkyl dimethicone/polycyclohexene oxide crosspolymer in cyclopentasiloxane.

18. The cosmetic composition of claim 17, wherein said second silicone elastomer is in the form of a powder.

19. The cosmetic composition of claim 17, wherein said second silicone elastomer is spherical.

20. The cosmetic composition of claim 1, wherein said second silicone elastomer is dimethicone/vinyldimethicone crosspolymer or dimethicone/vinyldimethicone coated with silica.

21. The cosmetic composition of claim 17, wherein said second silicone elastomer is dimethicone/vinyldimethicone crosspolymer or dimethicone/vinyldimethicone coated with silica.

22. The cosmetic composition of claim 1 or 12, further comprising at least one emollient provided in an amount of up to about 80% by weight.

23. The cosmetic composition of claim 22, wherein said emollient is provided in an amount of up to about 40% by weight.

24. The cosmetic composition of claim 23, wherein said emollient is provided in an amount of up to about 20% by weight.

25. A cosmetic base comprising: a cosmetic base comprising an anhydrous mixture of an effective amount of at least one first non-emulsifying, gellable silicone elastomer ranging from about 0.1 to about 40% by weight of dry elastomer; an effective amount of at least one second non-emulsifying silicone elastomer wherein said second silicone elastomer is nonsustainable and nonpilling and present in an amount of about 0.1 to about 40% by weight of dry elastomer; at least one non-aqueous solvent; and an effective amount of at least one water insoluble structuring agent which is compatible with said solvent and which has a melting point of between about 45 and about 95° C., wherein at least one of G'/G", measured at a frequency of 100 rad/s ranges from about 1 to about 100, G'/G", measured at a frequency of 0.1 rad/s ranges from about 0.1 to about 100 or the dynamic viscosity ranges from about $1\times10^1$ to about $9\times10^6$ Pa·s, and wherein the dynamic viscosity measured at a frequency of 0.1 rad/s is from about $1\times10^3$ to about $1\times10^6$ Pa·s., and wherein the cosmetic base is in the form of a mousse and wherein the cosmetic base is free from any emulsifying silicone elastomer.

26. The cosmetic base of claim 25, wherein G'/G", measured at a frequency of 100 rad/s ranges from about 1.2 to about 50, G'/G", or when measured at a frequency of 0.1 rad/s ranges from about 1 to about 50.

27. The cosmetic composition of claim 1, wherein G'/G", measured at a frequency of 100 rad/s ranges from about 1.3 to about 25, G'/G", or when measured at a frequency of 0.1 rad/s ranges from about 2.5 to about 25.

* * * * *

UNITED STATES PATENT AND TRADEMARK OFFICE
CERTIFICATE OF CORRECTION

PATENT NO.        : 8,394,394 B2
APPLICATION NO.   : 11/138940
DATED             : March 12, 2013
INVENTOR(S)       : Nathalie Geffroy-Hyland, Mohamed Kanji and Hy Si Bui Page 1 of 1

It is certified that error appears in the above-identified patent and that said Letters Patent is hereby corrected as shown below:

In the Specification
Column 4, line 4, "Pa·s" should read -- Pa.s --.
Column 11, line 61, "Pa·s" should read -- Pa.s --.
Column 11, line 62, "Pa·s" should read -- Pa.s --.
Column 11, line 63, "Pa·s" should read -- Pa.s --.
Column 11, line 65, "Pa·s" should read -- Pa.s --.
Column 12, line 1, "Pa·s" should read -- Pa.s --.
Column 12, line 4, "Pa·s" should read -- Pa.s --.
Column 12, line 7, "Pa·s" should read -- Pa.s --.
Column 12, line 10, "Pa·s" should read -- Pa.s --.

In the Claims
Column 19, line 40, "Pa·s" should read -- Pa.s --.
Column 20, line 3, "Pa·s" should read -- Pa.s --.
Column 20, line 21, "Pa·s" should read -- Pa.s --.
Column 22, line 1, "Pa·s" should read -- Pa.s --.
Column 22, line 3, "Pa·s" should read -- Pa.s --.

Signed and Sealed this
Thirty-first Day of March, 2015

Michelle K. Lee
*Director of the United States Patent and Trademark Office*